United States Patent [19]

Wyatt et al.

[11] Patent Number: 4,751,080

[45] Date of Patent: Jun. 14, 1988

[54] VACCINE AGAINST ROTAVIRUS DISEASES

[75] Inventors: Richard G. Wyatt, Potomac; Albert Z. Kapikian, Rockville; Robert M. Chanock, Bethesda; Karen Midthun, Sharpsburg; Jorge Flores; Yasutaka Hoshino, both of Bethesda, all of Md.

[73] Assignee: The United States of America as represented by the Department of Health and Human Services, Washington, D.C.

[21] Appl. No.: 79,940

[22] Filed: Jul. 31, 1987

Related U.S. Application Data

[62] Division of Ser. No. 769,074, Aug. 26, 1985, Pat. No. 4,704,275.

[51] Int. Cl.⁴ .................... A61K 39/12; A61K 39/15
[52] U.S. Cl. ...................................... 424/89; 435/235
[58] Field of Search ........................ 424/89; 435/235

[56] References Cited

U.S. PATENT DOCUMENTS 4,704,275 11/1987 Wyatt et al. .................... 424/89

OTHER PUBLICATIONS

Midthun et al. J. Virol. 53(3): 949–954 Mar. 1985.
Losonsky et al. Pediatr. Infect. Dis. 5(1): 25–29 Jan.–Feb. 1986.
Anderson et al. J. Infect. Dis. 153(5): 823–831 May 1986.
Vesikar et al. J. Infect. Dis. 153(5): 832–839 May 1986.
Rennels et al. Pediatr. Infect. Dis. 5(5): 587–588 Sep.–Oct. 1986.
Perez-Schael et al. J. Infect. Dis. 155(2): 334–338 Feb. 1987.
Baum et al. J. Infect. Dis. 155(2): 337 Feb. 1987.
Flores et al. Lancet 1(8538): 882–884 Apr. 18, 1987.
Rennels et al. Pediatr. Infect. Dis. J. 6(3): 260–264 Mar. 1987.

*Primary Examiner*—Shep K. Rose
*Attorney, Agent, or Firm*—Holman & Stern

[57] ABSTRACT

The present invention discloses a vaccine for the prevention of rotavirus caused diseases in humans. The vaccine is prepared from attenuated, immunogenic rhesus rotavirus which has been characterized to be antigenically similar, if not identical, to human rotavirus serotype 3.

2 Claims, 1 Drawing Sheet

VACCINE AGAINST ROTAVIRUS DISEASES

This is a divisional of application Ser. No. 769,074 filed Aug. 26, 1985, now U.S. Pat. No. 4,704,275.

BACKGROUND OF THE INVENTION

1. Technical Field

The present invention is related to a vaccine against rotavirus diseases. More particularly, the invention is related to the use of a live rhesus rotavirus attenuated in humans and which can be used as a vaccine in humans to prevent or control diseases caused by human rotaviruses.

2. State of the Art

Diarrheal disease is an important cause of morbidity in infants and young children in developed countries and is a major cause of morbidity and mortality in the same age group in developing countries. The extent of the problem of gastroenteritis in the United States was highlighted during a 10-year study of a group of Cleveland families in which infectious gastroenteritis was found to be the second most common disease experience, accounting for 16% of approximately 25,000 illnesses. The toll from diarrheal diseases in the developing countries is even more staggering. It has been estimated that in Asia, Africa, and Latin America 3–5 billion cases of diarrhea and 5–10 million diarrhea-associated deaths occur each year. In addition, diarrhea ranked first in the categories of frequency of disease and mortality. Moreover, from a summary of selected studies, it was estimated that 744 million to 1 billion episodes of diarrhea and 4.6 million deaths from diarrhea occur in children under 5 years of age in these regions, excluding China.

The discovery in 1972 of the 27-nm Norwalk virus and its association with epidemic viral gastroenteritis in older children and adults and the discovery in 1973 of the 70-nm human rotavirus and its association with gastroenteritis in infants and young children represent major recent advances in the long and elusive search for etiologic agents of acute infectious nonbacterial gastroenteritis. Rotaviruses have emerged as the single most important etiologic agents of serious diarrheal illness of infants and young children under 2 years of age in almost all developed and developing countries where appropriate studies have been performed. In most populations studied, rotaviruses have been associated with 35–50% of severe diarrheal disease occurring in infants and children under 2 years of age, who require hospitalization.

It is clear from a number of studies that rotaviruses are responsible for a significant proportion of serious diarrheal illness. Hence, a rotavirus vaccine is an obvious necessity in both the developing and the developed countries as a prophylactic measure against rotavirus diseases.

Several approaches to the development of a live rotavirus vaccine have been pursued. Two approaches that have been evaluated in humans include (1) the use of a live attenuated human rotavirus strain and (2) the use of a rotavirus strain of animal origin. The rationale for the second approach, the use of an animal rotavirus as a candidate vaccine for humans, has been suggested by several studies. First, animal and human rotaviruses share a common group antigen and second, calves immunized in utero with the bovine NCDV strain were resistant to challenge with a human rotavirus serotype-1 strain shortly after birth (Wyatt et al. 1979. *Science* 203: 548). As previously reported by Vesikari et al. (*Lancet* 1: 977 1984), oral administration of the bovine rotavirus NCDV strain (RIT 4637) induced resistance in infants and young children against moderate or severe diarrheal illness caused by human rotavirus.

It should be noted, however, that there are at least four known serotypes of human rotavirus. These are designated serotypes 1–4, respectively. Of these, serotypes 1 and 3 are the most important rotavirus serotypes with respect to human disease. In contrast, the bovine rotavirus used in some vaccines belongs to serotype 6 which has not yet been found in humans. Hence, a need obviously exists for the production of a vaccine which would provide immunity against infection from human rotaviruses belonging to all serotypes but more specifically against serotypes 1 and 3 which are the most pathogenic of the human rotaviruses.

SUMMARY OF THE INVENTION

It is, therefore, an object of the present invention to provide a vaccine against human rotaviruses.

It is a further object of the present invention to provide a vaccine for the prevention of rotavirus diseases using live, attenuated rhesus rotavirus.

It is yet another object of the present invention to provide a method of preventing or controlling rotavirus-caused diseases in humans by administering to humans an immunizing amount of live, attenuated serotype 3 (Strain MMU 18006) rhesus rotavirus in a sterile, nontoxic pharmaceutically acceptable carrier.

A still further object of the present invention is to provide a reassortant virus derived at least partly from the rhesus rotavirus as an immunogen for protecting humans against rotavirus diseases.

Other objects and advantages will become apparent as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 1 shows hybridization of rhesus rotavirus (RRV) to human rotavirus serotype 1, 2, 3, or 4. Single-stranded $^{32}$P-labeled mRNA transcripts of RRV were hybridized to the denatured genomic RNAs of RRV or human rotavirus serotype 1, 2, 3, or 4 (represented by strains D, DS-1, P, and ST3, respectively). In addition, $^{32}$P-labeled mRNA transcripts of human rotavirus strain D, DS-1, P, or ST3 were hybridized to their homologous genomic RNAs. The unlabelled genomic RNAs were placed in 1 mM EDTA, heated at 100° C. for 2 min, and then cooled in ice for 2–3 min. Hybridization buffer (100 mM NaCl, 50 mM Tris [pH 8], 0.1% SDS) containing approximately 10,000 cpm of the indicated $^{32}$P-labeled single-stranded RNA probe was added to the denatured cold RNAs and hybridization was allowed to take place at 65° C. for 14 hr. Hybridized RNAs were precipitated with 2.5 μg of tRNA by addition of 2–3 volumes of EtOH. After being held overnight at −20° C., the RNAs were pelleted (12,000 g), taken up in 20 μl of sample buffer, and electrophoresed on a 10% polyacrylamide gel for 14 hr at 20 mA. The gel was then subjected to autoradiography. Significant homology was not detected between the $^{32}$P-labeled RRV probe and genomic RNAs derived from any of the human rotavirus prototype strains;

FIG. 2 shows hybridization of denatured genomic RNAs from RRV (Rh-2) or bovine NCDV to a ss RNA probe from RRV. The hybrids were treated (+) or not treated (−) with S-1 nuclease before electrophoresis in a 12% gel. Homology between eight genes is demonstrated, however 3 of the 8 hybrid genes formed are susceptible to S-1 nuclease degradation, thus indicating a lack of complete homology. Further, by RNA-RNA hybridization in solution and by treatment of hybrids with S-1 nuclease, it was determined that a 60% homology exists between RRV and NCDV; and FIG. 3 shows analysis of the genotypes of human rotavirus strain DS-1 (serotype 2)×RRV (serotype 3) reassortant 240-2-1. This reassortant is serotype 2. Single-stranded $^{32}$P-labeled mRNA transcripts of RRV or DS-1 were hybridized to the denatured genomic RNAs of RRV, DS-1, or DS-1×RRV reassortant 240-2-1. The RNA-RNA hybrids were electrophoresed on a 10% polyacrylamide gel at 20 mA for 14 hr. The gel was then subjected to autoradiography. In the DS-1×RRV reassortant 240-2-1, the only gene of the human rotavirus parent that is present is the eighth gene that codes for VP7, the major neutralization protein. The remaining genes are derived from the RRV parent. The $^{32}$P-labeled DS-1 probe did not exhibit significant homology with the genomic RNAs of the RRV.

DETAILED DESCRIPTION OF INVENTION

The above objects and advantages of the present invention are achieved by a vaccine for the prevention of rotavirus diseases comprising an attenuated, live rhesus rotavirus belonging to serotype 3.

Figures 1, 2, 3:
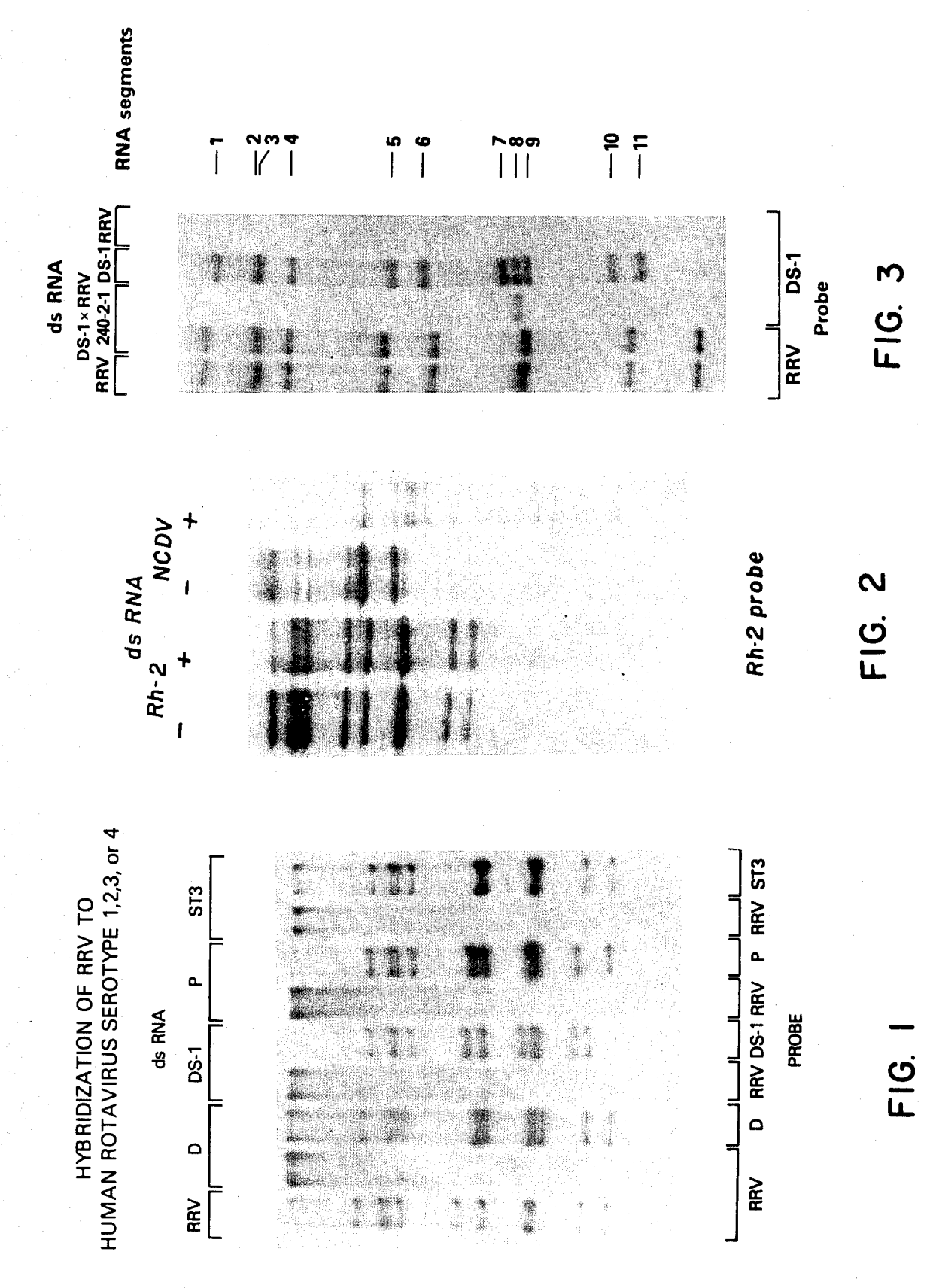

Heretofore, a vaccine prepared from a simian rotavirus strain has not been administered to humans. The rhesus rotavirus (RRV) provides a distinct advantage over other animal rotaviruses, particularly the bovine rotavirus, since the former but not the latter is antigenically similar, if not identical, to human rotavirus serotype 3, thereby being capable of inducing neutralizing antibodies against human rotavirus serotype 3. Results of gel electrophoresis shown in FIG. 2 establish the clear difference between the RRV and bovine rotavirus (NCDV).

It should be emphasized that in developing a safe and effective rotaviral vaccine, a thorough understanding is needed of the importance of the serotypic diversity and genetic characteristics of rotaviruses as well as the clinical and immunological responses of their human and animal hosts.

For the practice of the present invention, any similar or equivalent methods and materials as described herein can be used, but more preferred methods and materials are now presented. All publications mentioned hereunder are incorporated herein by reference.

Rhesus rotavirus strain (MMU18006 or S:USA:79:2) was isolated in primary cynomolgus monkey kidney cells (CMK) by Stuker et al (*J. Clin. Microbiol.* 11: 202 1980) from a stool sample collected one day after the onset of diarrhea in a 3.5 month old rhesus monkey designated MMU18006. This strain was passaged into primary African green (AG) MK cell cultures, followed by 3 successive plaque to plaque purifications in primary AGMK cell cultures and two additional passages in primary AGMK cell cultures. This seed virus was then passaged once in secondary AGMK cell cultures and then passaged serially 7 times into DBS-FRhL-2 cell cultures, a diploid cell strain derived from normal lung tissue of a rhesus monkey fetus (U.S. Pat. No. 4,040,905). DBS-FRhl-2 cells (Division of Biological Standards-Fetal Rhesus Lung-2) at passage 16 were obtained from K. H. Eckels, Walter Reed Army Institute of Research, Washington, D.C. Cells at passages 22 and 24 were used for production of pre-vaccine seed virus and vaccine virus, respectively. The virus was treated with a lipid-solvent, for instance, ether, after its fourth passage in DBS-FRhL-2 cells in order to inactivate any undetected adventitious enveloped viruses. Of course, ether could be replaced with other sterilizing agents or lipid solvents well known in the art such as chloroform and the like. The vaccine has a passage history as follows: CMK-2, AGMK-7, FRhL-2,-7.

The rhesus rotavirus (RRV) was chosen for clinical trials for three reasons. First, this virus is not known to be pathogenic in humans. Evidence of infection of humans with this virus under natural conditions has not been obtained. For example, in a survey of 92 rotaviruses derived from patients of diverse geographic origin, including the Indian subcontinent, the genes of almost all of these human rotaviruses hybridized under stringent conditions to labeled single-stranded (+) RNA transcripts ("probes") of a human serotype-1 or serotype-2 rotavirus, indicating that these viruses belonged to one of the two families of human rotavirus as defined by RNA-RNA hybridization (Flores et al. 1982. *Infect. Immun.* 37: 648). In contrast, genes of the 4 prototype human rotavirus serotypes and 12 other human rotavirus isolates from Bangladesh that hybridized to human rotavirus serotype-1 or serotype-2 probes, failed to form full-length, genomic-size hybrids when incubated with single-stranded (+) RNA transcripts prepared from RRV cores. Host restriction of RRV probably reflects the significant divergence of nucleotide sequence of its genes from that of the corresponding genes of human rotaviruses belonging to the four known serotypes. This divergence is illustrated by the failure of RRV single-stranded (+) RNA transcripts to form genomic-length hybrids when incubated with denatured genomic human rotavirus RNAs under stringent hybridization conditions (FIG. 1).

Second, the major neutralization protein (VP7) of RRV is very closely related antigenically to the corresponding protein of the human rotavirus serotype 3 (*Hoshino et al,* 1984, J. Inf. Dis. 149: 694–702) which is the second most important rotavirus serotye with respect to human disease (Table 1). RRV appears to be similar, if not identical, to human rotavirus serotype 3 in reciprocal neutralization tests.

TABLE 1

| Antigenic Relationships of RRV (Strain MMU 18006) with Four Human Rotavirus Serotypes by Plaque Reduction Neutralization (PRN) | | | | | |
|---|---|---|---|---|---|
| | 60% PRN antibody titer (reciprocal) of hyperimmune antiserum to indicated rotavirus | | | | |
| Rotavirus strain | Wa (type 1) | DS-1 (type 2) | P (type 3) | St. Thomas 3 (type 4) | RRV (MMU 18006) |
| Human serotype 1 (Wa) | ≥81920 | <80 | 2560 | 160 | <80 |

TABLE 1-continued

Antigenic Relationships of RRV (Strain MMU 18006) with Four Human Rotavirus Serotypes by Plaque Reduction Neutralization (PRN)

| | 60% PRN antibody titer (reciprocal) of hyperimmune antiserum to indicated rotavirus | | | | |
|---|---|---|---|---|---|
| Rotavirus strain | Wa (type 1) | DS-1 (type 2) | P (type 3) | St. Thomas 3 (type 4) | RRV (MMU 18006) |
| Human serotype 2 (DS-1) | <80 | 10240 | <80 | <80 | <80 |
| Human serotype 3 (P) | 640 | <80 | 81920 | 640 | 40960 |
| Human serotype 4 (St. Thomas 3) | 160 | <80 | <80 | 40960 | <80 |
| RRV (MMU 18006)* | <80 | <80 | >81920 | <80 | >81920 |

Homologous values are underlined.

Third, RRV grows to high titer in primary simian tissue culture and has been adapted to growth in DBS-FRhL-2 cells, a semicontinuous simian diploid cell strain. This property offers a considerable advantage because adventitious agents occur with high frequency in primary monkey kidney cell cultures in which bovine rotavirus, for instance, is cultured.

RRV grown in DBS-FRhL-2 cells has been evaluated in 52 individuals of progressively younger age (Table 2). The volunteers who participated in these studies possessed a varying level of prevaccination serum-neutralizing antibodies for RRV. Two of the volunteers possessed a very low level of serum-neutralizing antibodies (i.e., 1:40), whereas one had a titer of <1:20. In previous rotavirus volunteer studies, it was observed that susceptibility correlated with a lower titer of serum antibodies.

Each of 31 adult volunteers was given 1 ml of the RRV vaccine orally at a dose of $10^{6.0}$ pfu. None of the adult volunteers became ill, but 94% developed a serologic response to rotavirus and 84% developed a neutralizing antibody response to RRV (Table 2). The high frequency of seroresponse was surprising in view of the fact that all but one of the volunteers possessed RRV antibodies prior to administration of the virus. In addition, 65% of the test subjects receiving the vaccines developed a rise in neutralizing antibodies to at least one of the other three human rotavirus serotypes, i.e., serotypes 1, 2, or 4 (Table 3). Heterotypic neutralizing antibody responses were observed most often in individuals with a low level of prevaccination heterotypic antibodies and, as expected, was most often associated with a seroresponse to RRV. Virus shedding was not detected by immunoassay (ELISA) of stools from adult volunteers; however, small amounts of virus were recovered in tissue culture (MA104 cells: a cell line derived from fetal rhesus monkey kidney) from about 50% of the infected individuals.

TABLE 3

Serum Neutralizing Antibody (NAB) Responses to Heterotypic Rotaviruses in Volunteers Administered the RRV-1 (Serotype 3) Vaccine

| | Heterotypic ≧ fourfold serum NAB rise to indicated rotavirus | | | | | | | |
|---|---|---|---|---|---|---|---|---|
| | serotype 1 (Wa) | | serotype 2 (DS-1) | | serotype 4 (St. Thomas 3) | | bovine UK | |
| Group (no.) | no. tested | no. with rise | no. tested | no. with rise | no. tested | no. with rise | no. tested | no. with rise |
| Young adults (31)[a] | 16 | 8 (50%) | 31 | 20 (65%) | 11 | 4 (36%) | 11 | 6 (55%) |

[a]Excludes one volunteer with intercurrent rotavirus infection.

Twenty-one children (2–12 years of age) were also evaluated for their response to RRV following oral administration of this virus. None developed an illness significantly associated with the RRV inoculum (Table 3). Eight of ten children tested developed a seroresponse to rotavirus. RRV was detected by ELISA in the stools of three children. A larger proportion of children was shown to shed rotavirus in their stools when tissue culture was used for recovery of virus.

These results indicate that RRV is a useful vaccine strain for protecting humans against rotavirus diseases because it is satisfactorily attenuated yet antigenic. Also, 65% of the volunteers developed heterotypic serum-neutralizing antibodies against at least one other

TABLE 2

Response of Individuals to Oral Administration of RRV Vaccine (Strain MMU 18006)

| | | Prevaccination serum NAB titer (reciprocal) to RRV by 60% PRN (or by tube neutralization) | | No. with Indicated clinical response associated with vaccination | | | Serologic response (≧ fourfold) to rotavirus in pre- and postvaccination sera | | | | | |
|---|---|---|---|---|---|---|---|---|---|---|---|---|
| | | | | | | | neutralization of RRV | | CF and/or IAHA | | any test | |
| Group | No. | GMT | range | diarrhea | vomiting | fever | no tested | no with response | no tested | no with response | no tested | no with response |
| Young adults | 31[a] | 489 (12) | <20–1280 (<4–32) | 0 | 0 | 0 | 31 | 24 (77%) | 31 | 26 (84%) | 31 | 29 (94%) |
| Children (2-12 yr) | 21 | 485 (25)[b] | 40–2560(8–80) | 0 | 1[c] | 2[c] | 6 | 3 (50%) | 10 | 8 (80%) | 10 | 8 (80%) |

Passage history: Cynomolgus MK2. AGMK7,FRhL-27 (designated RRV-1)
[a]Excludes one volunteer with intercurrent rotavirus infection
[b]Includes 20 (8) children
[c]Among the 20 control children, 3 developed fever (≧101° F.) within the week following administration of placebo (one of the 3 also had an episode of vomiting)

serotype, thereby indicating a broad spectrum of antigenicity against human rotaviruses.

Additionally, RRV may also be useful as a donor of attenuating genes that can be transferred to reassortant viruses that bear the major neutralization protein (VP7) of a human rotavirus belonging to serotype 1, 2, or 4. This may be important if heterotypic immunity induced by RRV itself is found to be less than optimal. For example, a heterotypic strain such as NCDV or RRV may not induce satisfactory protection against all human rotavirus serotypes or such protection may be transitory. If this proves to be the case, it may be necessary to use rotavirus reassortants that provide homotypic immunity for each of the human rotavirus serotypes. Such single-gene substitution reassortants have been prepared for serotype-1, serotype-2 and serotype 4 human rotaviruses (Midthun et al. 1985 *J. Virol.*). These reassortants possess ten RRV genes and a single human rotavirus gene, the one that codes for neutralization specificity. An example of such a reassortant is shown in FIG. 3 which illustrates an RRV×DS-1 (human serotype 2) reassortant that contains only a single human rotavirus gene, which codes for the major neutralizing antigen VP7 of the human rotavirus serotype 2.

It is likely that such single-gene substitution reassortants will induce immunity to viruses belonging to the serotype of their human rotavirus parent while retaining the attenuation of their RRV parent. If additional human rotavirus serotypes emerge in the future and prove to be important causes of disease, they too could be attenuated by transferring the RRV genes to reassortants bearing the VP7 gene of the newly recognized serotype. Such manipulations, of course, substantially enhance the utility of the RRV.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of protecting humans from rotavirus diseases comprising administering to a human an immunizing amount of live, attenuated serotype 3 rhesus rotavirus strain MMU 18006 in a sterile, nontoxic pharmaceutically acceptable carrier, wherein said rotavirus is a reassortant virus derived at least partly from the rhesus rotavirus.

2. A vaccine for the prevention of rotavirus diseases in humans comprising live, attenuated serotype 3 rhesus rotavirus strain MMU 18006 in a suitable sterile, nontoxic physiological medium, wherein said rotavirus is a reassortant virus derived at least partly from the rhesus rotavirus.

* * * * *